(12) United States Patent
Wang et al.

(10) Patent No.: US 7,964,210 B2
(45) Date of Patent: Jun. 21, 2011

(54) DEGRADABLE POLYMERIC IMPLANTABLE MEDICAL DEVICES WITH A CONTINUOUS PHASE AND DISCRETE PHASE

(75) Inventors: Yunbing Wang, Mountain View, CA (US); David C. Gale, San Jose, CA (US); Bin Huang, Pleasanton, CA (US); Syed F. A. Hossainy, Fremont, CA (US); Vincent J. Gueriguian, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1250 days.

(21) Appl. No.: 11/395,048

(22) Filed: Mar. 31, 2006

(65) Prior Publication Data
US 2007/0231365 A1 Oct. 4, 2007

(51) Int. Cl.
*A61F 2/02* (2006.01)

(52) U.S. Cl. ........ 424/426; 424/422; 424/423; 424/484; 424/486; 623/1.15

(58) Field of Classification Search .................... None
See application file for complete search history.

(56) References Cited

U.S. PATENT DOCUMENTS

| | | | |
|---|---|---|---|
| 3,636,956 A * | 1/1972 | Schneider | 606/224 |
| 3,687,135 A | 8/1972 | Stroganov et al. | |
| 3,839,743 A | 10/1974 | Schwarcz | |
| 3,900,632 A | 8/1975 | Robinson | |
| 4,104,410 A | 8/1978 | Malecki | |
| 4,110,497 A | 8/1978 | Hoel | |
| 4,321,711 A | 3/1982 | Mano | |
| 4,346,028 A | 8/1982 | Griffith | |
| 4,596,574 A | 6/1986 | Urist | |
| 4,599,085 A | 7/1986 | Riess et al. | |
| 4,612,009 A | 9/1986 | Drobnik et al. | |
| 4,633,873 A | 1/1987 | Dumican et al. | |
| 4,656,083 A | 4/1987 | Hoffman et al. | |
| 4,718,907 A | 1/1988 | Karwoski et al. | |
| 4,722,335 A | 2/1988 | Vilasi | |
| 4,723,549 A | 2/1988 | Wholey et al. | |
| 4,732,152 A | 3/1988 | Wallstén et al. | |
| 4,733,665 A | 3/1988 | Palmaz | |
| 4,739,762 A | 4/1988 | Palmaz | |
| 4,740,207 A | 4/1988 | Kreamer | |
| 4,743,252 A | 5/1988 | Martin, Jr. et al. | |
| 4,744,365 A * | 5/1988 | Kaplan et al. | 606/230 |
| 4,768,507 A | 9/1988 | Fischell et al. | |
| 4,776,337 A | 10/1988 | Palmaz | |
| 4,800,882 A | 1/1989 | Gianturco | |
| 4,816,339 A | 3/1989 | Tu et al. | |
| 4,818,559 A | 4/1989 | Hama et al. | |
| 4,844,854 A | 7/1989 | Kaplan et al. | |
| 4,850,999 A | 7/1989 | Planck | |
| 4,877,030 A | 10/1989 | Beck et al. | |
| 4,878,906 A | 11/1989 | Lindemann et al. | |
| 4,879,135 A | 11/1989 | Greco et al. | |
| 4,886,062 A | 12/1989 | Wiktor | |
| 4,902,289 A | 2/1990 | Yannas | |
| 4,977,901 A | 12/1990 | Ofstead | |
| 4,994,298 A | 2/1991 | Yasuda | |
| 5,019,090 A | 5/1991 | Pinchuk | |
| 5,028,597 A | 7/1991 | Kodama et al. | |
| 5,059,211 A | 10/1991 | Stack et al. | |
| 5,062,829 A | 11/1991 | Pryor et al. | |
| 5,084,065 A | 1/1992 | Weldon et al. | |
| 5,085,629 A | 2/1992 | Goldberg et al. | |
| 5,100,429 A | 3/1992 | Sinofsky et al. | |
| 5,104,410 A | 4/1992 | Chowdhary | |
| 5,108,417 A | 4/1992 | Sawyer | |
| 5,108,755 A | 4/1992 | Daniels et al. | |
| 5,112,457 A | 5/1992 | Marchant | |
| 5,123,917 A | 6/1992 | Lee | |
| 5,156,623 A | 10/1992 | Hakamatsuka et al. | |
| 5,163,951 A | 11/1992 | Pinchuk et al. | |
| 5,163,952 A | 11/1992 | Froix | |
| 5,163,958 A | 11/1992 | Pinchuk | |
| 5,167,614 A | 12/1992 | Tessmann et al. | |
| 5,192,311 A | 3/1993 | King et al. | |
| 5,197,977 A | 3/1993 | Hoffman, Jr. et al. | |
| 5,234,456 A | 8/1993 | Silvestrini | |
| 5,234,457 A | 8/1993 | Andersen | |
| 5,236,447 A | 8/1993 | Kubo et al. | |
| 5,279,594 A | 1/1994 | Jackson | |

(Continued)

FOREIGN PATENT DOCUMENTS

EP 0 108 171 5/1984

(Continued)

OTHER PUBLICATIONS

Dobrzyski, et al., Biomacromolecules, vol. 6, No. 1, 2005.*

(Continued)

*Primary Examiner* — Robert A Wax
*Assistant Examiner* — William Craigo
(74) *Attorney, Agent, or Firm* — Squire, Sanders & Dempsey (US) LLP (57) ABSTRACT

The invention provides an implantable medical device comprising: a structural element, wherein the structural element includes: a continuous phase comprising a first polymer; a discrete phase within the continuous phase, wherein the discrete phase has a second polymer including discrete phase segments; and anchor segments that have substantially the same chemical make up as the first polymer of the continuous phase; wherein at least some of the anchor segments have partially or completely phase-separated from the discrete phase into the continuous phase.

53 Claims, 3 Drawing Sheets

U.S. PATENT DOCUMENTS

| | | | |
|---|---|---|---|
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,641,501 A | 6/1997 | Cooper et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,150,630 A | 11/2000 | Perry et al. |
| 6,153,252 A | 11/2000 | Hossainy et al. |
| 6,159,951 A | 12/2000 | Karpeisky et al. |
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |

| | | |
|---|---|---|
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,818,063 B1 | 11/2004 | Kerrigan |
| 6,846,323 B2 | 1/2005 | Yip et al. |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0062148 A1 | 5/2002 | Hart |
| 2002/0065553 A1 | 5/2002 | Weber |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2003/0033001 A1 | 2/2003 | Igaki |
| 2003/0093107 A1 | 5/2003 | Parsonage et al. |
| 2003/0100865 A1 | 5/2003 | Santini, Jr. et al. |
| 2003/0105518 A1 | 6/2003 | Dutta |
| 2003/0105530 A1 | 6/2003 | Pirhonen |
| 2003/0171053 A1 | 9/2003 | Sanders |
| 2003/0187495 A1 | 10/2003 | Cully et al. |
| 2003/0208259 A1 | 11/2003 | Penhasi |
| 2003/0209835 A1 | 11/2003 | Chun et al. |
| 2003/0226833 A1 | 12/2003 | Shapovalov et al. |
| 2003/0236565 A1 | 12/2003 | DiMatteo et al. |
| 2004/0093077 A1 | 5/2004 | White et al. |
| 2004/0098095 A1 | 5/2004 | Burnside et al. |
| 2004/0111149 A1 | 6/2004 | Stinson |
| 2004/0127970 A1 | 7/2004 | Saunders et al. |
| 2004/0143317 A1 | 7/2004 | Stinson et al. |
| 2004/0167610 A1 | 8/2004 | Fleming, III |

FOREIGN PATENT DOCUMENTS

| | | |
|---|---|---|
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| EP | 1491221 A1 * | 12/2004 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 2004/023985 | 3/2004 |

OTHER PUBLICATIONS

Whelan, Polymer Technology Dictionary, 1994.*
U.S. Appl. No. 10/317,435, filed Dec. 11, 2002, Hossainy et al.
Anonymous, *Bioabsorbable stent mounted on a catheter having optical coherence tomography capabilities*, Research Disclosure, Sep. 2004, pp. 1159-1162.
Ansari, *End-to-end tubal anastomosis using an absorbable stent*, Fertility and Sterility, vol. 32(2), pp. 197-201 (Aug. 1979).
Ansari, *Tubal Reanastomosis Using Absorbable Stent*, International Journal of Fertility, vol. 23(4), pp. 242-243 (1978).
Bull, *Parylene Coating for Medical Applications*, Medical Product Manufacturing News 18, 1 pg. (Mar. 1993).
Casper et al., *Fiber-Reinforced Absorbable Composite for Orthopedic Surgery*, Polymeric Materials Science and Engineering, vol. 53 pp. 497-501 (1985).
Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).
Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules, vol. 2, pp. 430-441 (2001).

Hahn et al., *Biocompatibility of Glow-Discharge-Polymerized Films and Vacuum-Deposited Parylene*, J Applied Polymer Sci, vol. 38, pp. 55-64 (1984).

Hahn et al., *Glow Discharge Polymers as Coatings for Implanted Devices*, ISA, pp. 109-111 (1981).

He et al., *Assessment of Tissue Blood Flow Following Small Artery Welding with an Intraluminal Dissolvable Stent*, Microsurgery, vol. 19(3), pp. 148-152 (1999).

Kelley et al., *Totally Resorbable High-Strength Composite Material*, Advances in Biomedical Polymers, vol. 35, pp. 75-85 (1987).

Kubies et al., *Microdomain Structure in polylactide-block-poly(ethylene oxide) copolymer films*, Biomaterials, vol. 21, pp. 529-536 (2000).

Kutryk et al., *Coronary Stenting: Current Perspectives*, a companion to the Handbook of Coronary Stents, pp. 1-16 (1999).

Martin et al., *Enhancing the biological activity of immobilized osteopontin using a type-1 collagen affinity coating*, J. Biomed. Mater. Res., vol. 70A, pp. 10-19 (2004).

Mauduit et al., *Hydrolytic degradation of films prepared from blends of high and low molecular weight poly(DL-lactic acids)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., vol. 1(4), pp. 438-448 (Jul./Aug. 1990).

Nichols et al., *Electrical Insulation of Implantable Devices by Composite Polymer Coatings*, ISA Transactions, vol. 26(4), pp. 15-18 (1987).

International Search Report for PCT/US2007/006527, filed Mar. 14, 2007, mailed Nov. 27, 2007, 6 pgs.

Hamley et al., "Crystallization in Poly(L-lactide)-b-poly(ε-caprolactone) Double Crystalline Diblock Copolymers: A Study Using X-ray Scattering, Differential Scanning Calorimetry, and Polarized Optical Microscopy", Macromolecules 38, pp. 463-472 (2005).

Peuster et al., *A novel approach to temporary stenting: degradable cardiovascular stents produced from corrodible metal-results 6-18 months after implantation into New Zealand white rabbits*, Heart, vol. 86, pp. 563-569 (2001).

Pietrzak et al., *Bioabsorbable Fixation Devices: Status for the Craniomaxillofacial Surgeon*, J. Craniofaxial Surg., vol. 2, pp. 92-96 (1997).

Pietrzak et al., *Bioresorbable implants—practical considerations*, Bone, vol. 19, No. 1, Supplement Jul. 1996, pp. 109S-119S.

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, vol. 79(2), pp. 445-457 (Feb. 1989).

Schmidt et al., *Long-Term Implants of Parylene-C Coated Microelectrodes*, Med & Biol Eng & Comp, vol. 26(1), pp. 96-101 (Jan. 1988).

Spagnuolo et al., *Gas 1 is induced by VE-cadherin and vascular endothelial growth factor and inhibits endothelial cell apoptosis*, Blood, vol. 103, pp. 3005-3012 (2004).

Tamai et al., *Initial and 6-Month Results of Biodegradable Poly-l-Lactic Acid Coronary Stents in Humans*, Circulation, pp. 399-404 (Jul. 25, 2000).

Tsuji et al., *Biodegradable Polymeric Stents*, Current Interventional Cardiology Reports, vol. 3, pp. 10-17 (2001).

Völkel et al., *Targeting of immunoliposomes to endothelial cells using a single—chain Fv fragment directed against human endoglin (CD105)*, Biochimica et Biophysica Acta 1663, pp. 158-166 (2004).

Van Vlack, *Elements of Materials Science and Engineering*, University of Michigan, pp. 270-271, 1989, 4 pgs.

Von Recum et al., *Degradation of polydispersed poly(L-lactic acid) to modulate lactic acid release*, Biomaterials, vol. 16, pp. 441-445 (1995).

Yau et al., Modern Size-Exclusion Liquid Chromatography, Wiley-Interscience Publication, IX-XV (1979).

\* cited by examiner

DEGRADABLE POLYMERIC IMPLANTABLE MEDICAL DEVICES WITH A CONTINUOUS PHASE AND DISCRETE PHASE

BACKGROUND OF THE INVENTION

1. Field of the Invention

This invention relates to a degradable polymeric implantable medical device.

2. Description of the State of the Art

This invention relates generally to implantable medical devices having a range of mechanical and therapeutic requirements during use. In particular, the invention relates to radially expandable endoprostheses that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty. "Restenosis" refers to the reoccurrence of stenosis in a blood vessel or heart valve after it has been subjected to angioplasty or valvuloplasty.

The treatment of a diseased site or lesion with a stent involves both delivery and deployment of the stent. "Delivery" refers to introducing and transporting the stent through a bodily lumen to the treatment site in a vessel. "Deployment" corresponds to the expanding of the stent within the lumen at the treatment site. Delivery and deployment of a stent are accomplished by positioning the stent at one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand.

The stent must be able to satisfy several mechanical requirements. First, the stent must be capable of withstanding the structural loads, namely radial compressive forces, imposed on the stent as it supports the walls of a vessel lumen. This requires a sufficient degree of strength and rigidity or stiffness. In addition to having adequate radial strength, the stent should be longitudinally flexible to allow it to be maneuvered through a tortuous vascular path and to enable it to conform to a deployment site that may not be linear or may be subject to flexure. The material from which the stent is constructed must allow the stent to undergo expansion which typically requires substantial deformation of portions of the stent. Once expanded, the stent must maintain its size and shape throughout its service life despite the various forces that may come to bear thereon, including the cyclic loading induced by the beating heart. Therefore, a stent must be capable of exhibiting relatively high toughness which corresponds to high strength and rigidity, as well as flexibility.

A stent is typically composed of scaffolding that includes a pattern or network of interconnecting structural elements or struts. The scaffolding can be formed of wires, tubes, or sheets of material rolled into a cylindrical shape. The scaffolding is designed to allow the stent to be radially expandable. The pattern is generally designed to maintain the longitudinal flexibility and radial rigidity required of the stent. Longitudinal flexibility facilitates delivery of the stent and radial rigidity is needed to hold open a bodily lumen. A medicated stent may be fabricated by coating the surface of either a metallic or polymeric scaffolding with a polymeric carrier that includes a bioactive agent. Polymeric scaffolding may also serve as a carrier of bioactive agent.

It may be desirable for a stent to be biodegradable. In many treatment applications, the presence of a stent in a body may be necessary for a limited period of time until its intended function, for example, maintaining vascular patency and/or drug delivery is accomplished. Thus, stents are often fabricated from biodegradable, bioabsorbable, and/or bioerodable materials such that they completely erode only after the clinical need for them has ended. In addition, a stent should also be capable of satisfying the mechanical requirements discussed above during the desired treatment time.

A polymeric implantable medical device should be mechanically stable throughout the range of stress experienced during use. Unfortunately, many polymers used for stent scaffoldings and coatings are relatively brittle under physiological conditions, e.g., at body temperature. Many polymers remain relatively brittle, and hence susceptible to mechanical instability such as fracturing while in the body. In addition to mechanical stability, a device should have a sufficiently rate of biodegradability or erosion as dictated by use.

SUMMARY

The invention provides an implantable medical device comprising: a structural element, wherein the structural element includes: a continuous phase comprising a first polymer; a discrete phase within the continuous phase, wherein the discrete phase has a second polymer including discrete phase segments; the second polymer further includes anchor segments that have the same or substantially the same chemical make up as the first polymer of the continuous phase, and at least some of the anchor segments have partially or completely phase-separated from the discrete phase into the continuous phase.

The invention also provides an implantable medical device, comprising a blend including: a structural element including: about 60 to about 99 wt % of a first polymer, wherein the first polymer forms a continuous phase; and about 1 to about 40 wt % of a second polymer, the second polymer forming a discrete phase within the continuous phase, wherein the second polymer has a $T_g$ below body temperature and comprises discrete-phase segments that degrade to acidic fragments, the second polymer also comprises anchor segments having the same or substantially the same chemical make up as the continuous phase, wherein the anchor segment has phase-separated out from the discrete phase into the continuous phase.

An implantable medical device, comprising a blend comprising: a structural element including: from about 60 to about 99 wt % of a first polymer, wherein the first polymer forms a continuous phase; about 0.2 to about 5 wt % of a second polymer, the second polymer forming a discrete phase within the continuous phase, the second polymer comprising discrete phase segments and anchor segments, wherein anchor segments have substantially the same chemical make up as the first polymer of the continuous phase and have phase-separated out from the discrete phase into the continuous phase; and about 1 to about 40 wt % of a third polymer comprising having a $T_g$ below body temperature consists essentially of discrete phase segments, wherein the third polymer degrades into fragments at least some of which are acidic.

The invention also provides an implantable medical device, comprising: about 60 to about 99 wt % of a first polymer having the chemical structure:

about 1 to about 40 wt % of a second polymer having the chemical structure:

$Z$ is a polymer with a $T_g$ below body temperature that degrades into fragments at least some of which are acidic; wherein:

the first polymer forms a continuous phase;

the "Z" polymer forms a discrete phase within the continuous phase; and, the "p" segment of the second polymer partially or completely phase-separates out from the discrete phase into the continuous phase.

The invention also provides a composition comprising: a continuous phase comprising a first polymer; a discrete phase within the continuous phase, wherein the discrete phase comprises a second polymer including discrete phase segments; the second polymer further includes anchor segments that have the same or substantially the same chemical make up as the first polymer of the continuous phase; and at least some of the anchor segments have partially or completely phase-separated from the discrete phase into the continuous phase.

The invention also provides a method of forming a copolymer comprising: mixing glycolide monomers, caprolactone monomers, and a solvent to form a solution, wherein the glycolide and caprolactone monomers react in the solution to form poly(glycolide-co-ε-caprolactone); and combining L-lactide monomers with the solution to allow the L-lactide monomers to react with the poly(glycolide-co-ε-caprolactone) to form poly(glycolide-co-ε-caprolactone)-b-poly(L-lactide).

A method of forming a copolymer comprising: mixing glycolide monomers, caprolactone monomers, and a solvent to form a solution, wherein the glycolide and caprolactone monomers react in the solution to form poly(glycolide-co-ε-caprolactone); combining L-lactide monomers with the solution to allow the L-lactide monomers to react with the poly(glycolide-co-ε-caprolactone) to form poly(glycolide-co-ε-caprolactone)-b-poly(lactide); combining L-lactide and glycolide monomers with the solution to allow the L-lactide and glycolide monomers to react with the poly(glycolide-co-ε-caprolactone) to form poly(glycolide-co-ε-caprolactone)-b-poly(L-lactide-co-glycolide); and combining L-lactide and glycolide monomers with the solution to allow the L-lactide and glycolide monomers to react with the poly(glycolide-co-ε-caprolactone) to form poly(glycolide-co-ε-caprolactone)-b-poly(lactide-co-glycolide).

BRIEF DESCRIPTION OF DRAWINGS

FIG. 1b depicts a view of a sidewall of a segment of a strut of FIG. 1a.

DETAILED DESCRIPTION

Various embodiments of the present invention relate to composite implantable medical devices configured to have particular mechanical properties such as strength and flexibility. Embodiments of the present invention also relate to composite devices with particular degradation characteristics. A composite implantable medical device is a device which is made up of two or more macroscopically distinct materials or phases that have different properties. The composite device as a whole may have desirable properties of two or more of the distinct materials or phases. Therefore, desirable mechanical and/or degradation properties in an implantable medical device may be obtained through the use of a polymer composite structure.

For the purposes of the present invention, the following terms and definitions apply:

The "glass transition temperature," $T_g$, of a polymer is the temperature at which the polymer's amorphous domains transform from a brittle vitreous state to a solid deformable or ductile state at atmospheric pressure. In other words, $T_g$ corresponds to the temperature where segmental motion starts in the polymer chains. When an amorphous or semicrystalline polymer is exposed to an increasing temperature, both the polymer's coefficient of expansion and heat capacity increase as the temperature is raised, indicating increased molecular motion. As the temperature is raised, the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility.

"Solvent" is defined as a substance capable of dissolving or dispersing one or more other substances or capable of at least partially dissolving or dispersing the substance(s) to form a uniform mixture at the molecular- or ionic-size level. It should be noted that some solvents can only dissolve, for example, glycolide monomers at high temperatures.

"Dissolve" refers to a substance passing into solution on a molecular scale with or without chemical breakdown of the substance.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). Compressive stress is a normal component of stress applied to materials resulting in their compaction (decrease in length).

"Expansion" or "compression" is defined as the increase or decrease in length of a sample of material when the sample is subjected to stress.

"Strain" refers to the amount of expansion or compression that occurs in a material at a given stress. Strain is expressed as a fraction or percentage of the original length, i.e., the change in length divided by the original length. Strain, therefore, is positive for expansion and negative for compression.

A property of a material that quantifies a degree of strain with applied stress is the modulus. "Modulus" may be defined as the ratio of a component of stress per unit area divided by the strain along the axis of the applied force. A material has both a tensile and a compressive modulus. A material with a relatively high modulus tends to be stiff or rigid. Conversely, a material with a relatively low modulus tends to be flexible. The modulus of a material depends on its molecular composition and structure, temperature, and the strain rate or rate of deformation. Below its $T_g$, a polymer tends to be brittle with a high modulus. As the temperature of a polymer is increased to above its $T_g$, its modulus decreases.

"Ultimate strength" or "strength" of a material refers to the maximum stress that a material will withstand prior to fracture. A material may have both a tensile and a compressive strength. Ultimate strength is calculated from the maximum load applied during a test divided by the original cross-sectional area.

"Toughness" is the amount of energy absorbed prior to fracture, or equivalently, the amount of work required to fracture a material. One measure of toughness is the area under a stress-strain curve from zero strain to the strain at fracture. The units of toughness are energy per unit volume of material. See, e.g., L. H. Van Vlack, "Elements of Materials Science and Engineering," pp. 270-271, Addison-Wesley (Reading, Pa., 1989).

A brittle material is a relatively stiff or rigid material that exhibits little or no plastic deformation. As stress is applied to a brittle material, it tends to fracture at a stress approximately equal to its ultimate strength, undergoing little or no plastic deformation in the process. A polymer below its $T_g$ tends to be brittle. In contrast, a ductile material under an applied stress exhibits both elastic and plastic deformation prior to fracture. Above its $T_g$, a polymer is ductile.

A fracture may be categorized as either ductile or brittle. A relatively low amount of energy is required to fracture brittle materials. Conversely, ductile materials can absorb a relatively high amount of energy prior to fracture. Therefore, ductile materials tend to exhibit a higher toughness than brittle materials. Toughness is a desirable characteristic in implantable medical devices.

Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants, artificial bone; prostheses, vascular grafts, self-expandable stents, balloon-expandable stents, stent-grafts, grafts, artificial heart valves and cerebrospinal fluid shunts.

"Use" of a stent includes manufacturing, assembling (e.g., crimping a stent on balloon), delivery of a stent through a bodily lumen to a treatment site, deployment of a stent at a treatment site, and treatment of a deployed stent. Both a scaffolding or substrate and a coating on a scaffolding experience stress. For example, during deployment, the scaffolding and/or coating of a stent can be exposed to stress caused by the radial expansion of the stent body. In addition, the scaffolding and/or coating may be exposed to stress when it is mounted on a catheter from crimping or compression of the stent. These stresses can cause the scaffolding and/or coating to fracture and the coating to tear and/or detach from the scaffolding. Failure of the mechanical integrity of the stent while the stent is in a patient can lead to serious consequences. For example, there is a risk of embolization caused by pieces of the polymeric scaffolding and/or coating breaking off from the stent.

Figure 1A:
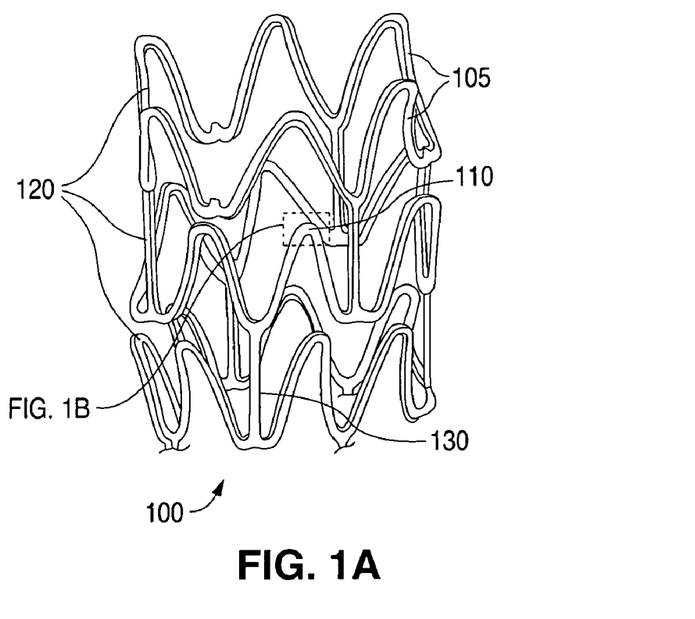
FIG. 1a depicts a stent made up of struts.

FIG. 1a depicts a stent 100 comprising struts 105. Stent 100 has interconnected cylindrical rings 120 connected by linking struts 130. The embodiments disclosed herein are not limited to stents or to the stent pattern depicted in FIG. 1a. In many treatment applications, implantable medical devices, such as a stent, are preferably relatively tough and flexible since devices have varied mechanical requirements during use, both before and during treatment.

An implantable medical device may be configured to degrade after implantation by fabricating the device either partially or completely from biodegradable polymers. Polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and may be gradually absorbed and eliminated by the body.

A biodegradable device may remain in the body until its intended function of, for example, maintaining vascular patency and/or drug delivery is accomplished. For biodegradable polymers used in coating applications, after the process of degradation, erosion, absorption has been completed, no polymer will remain on the stent. In some embodiments, very negligible traces or residue may be left behind. The duration is typically in the range of six to eighteen months, although other durations are possible.

Erosion rate of the polymer depends on a number of factors including, but not limited to, chemical composition, thickness, porosity, molecular weight, and degree of crystallinity. Several characteristics of the degradation process are important in designing biodegradable devices. These include average erosion rate, the erosion profile, the half-life of the degrading polymer, and mechanical stability of a device during the degradation process. A higher porosity increases degradation rates. Molecular weight tends to be inversely proportional to degradation rate. Higher crystallinity tends to result in a lower degradation rate. Amorphous regions of a polymer have a higher degradation rate than crystalline regions.

Biodegradation refers generally to changes in physical and chemical properties that occur in a polymer upon exposure to bodily fluids as in a vascular environment. The changes in properties may include a decrease in molecular weight, deterioration of mechanical properties, and decrease in mass due to erosion or absorption.

A decrease in molecular weight during biodegradation is caused by hydrolysis and/or metabolic processes. In general, hydrolysis is a chemical process in which a molecule is cleaved into two parts by the addition of a molecule of water. With respect to a bioabsorbable polymer such as PLLA, water takes part in the hydrolysis of ester bonds in the polymer backbone which leads to the formation of water-soluble fragments. Consequently, the rate of degradation of a biodegradable polymer is strongly dependent on the concentration of water in the polymer. A higher concentration of water in a polymer can lead to a faster rate of hydrolysis, tending to result in a shorter degradation time of a device made from the polymer.

Polymers that may be used to fabricate, coat, or modify an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(L-lactide-co-ε-caprolactone), poly(trimethylene carbonate), polyester amide, poly (glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

Many biodegradable polymers used for stent scaffoldings and coatings are relatively brittle under biological conditions. This is particularly true for biodegradable polymers with a $T_g$ above a body temperature, such as poly (L-lactide) ("PLLA"). The polymer remains relatively brittle and susceptible to mechanical instability while in the body. Therefore, for polymers like PLLA that are brittle under biological conditions, the fracture toughness is lower than desirable in implantable medical devices.

Another deficiency of some biodegradable polymers, such as PLLA, is that the degradation rate is slow and results in a degradation time outside the desired range. A preferred degradation is from six to twelve months. As described above, increasing the equilibrium content of moisture in a biodegradable polymer that degrades by hydrolysis can increase the degradation rate of a polymer. Various embodiments of the present invention include increasing the equilibrium moisture content in a polymer of a device to accelerate the degradation rate.

One way to increase fracture toughness in brittle polymers such as PLLA under biological conditions is to blend PLLA with a polymer having relatively high fracture toughness under biological conditions. Polymers tend to phase separate out into a discrete phase and continuous phase. To ensure good energy transfer between interfaces, it is important that there be sufficient bonding or adhesion between the continuous phase and discrete phase (See, Y. Wang, etc. Journal of Polymer Science Part A: Polymer Chemistry, 39, 2001, 2755-2766). Insufficient adhesion can be particularly problematic when the continuous phase and the discrete phase differ substantially in microstructure.

Biodegradable Polymers of high fracture toughness include polycaprolactone (PCL) and poly(tetramethyl carbonate) (PTMC). However, PCL and PTMC are immiscible in many polymers such as PLLA. A mixture of PLLA and either PCL or PTMC tends to separate into a PLLA continuous phase and PCL or PTMC discrete phase. Poor interfacial adhesion between the discrete and continuous phase works against the increase of fracture toughness in a polymer blend.

The polymer blends according to the invention have good adhesion between the discrete phase and the continuous phase, enabling various polymers to be mixed together for their respective beneficial properties. Good adhesion of polymers enables a polymer blend to absorb energy because there is good energy transfer at the interface, or contact plane between the periphery particles of each phase. High interfacial energy transfer between phases tends to be achieved because the discrete phase is well blended or dispersed into the continuous phase, and there is good adhesion between discrete and continuous phase. Thus, the polymer blends according to the invention tends to absorb energy of a crack, thus, inhibiting crack propagation, and increasing fracture toughness of the blends.

Certain polymer blends of the invention have been found to have an increase in fracture toughness together with an increase in degradation rate. In some embodiments, the blend may include a first polymer that is relatively brittle under biological conditions and a relatively slow degradation rate slower. The first polymer may be blended with a second polymer having discrete phase segments and anchor segments that have substantially the same or the same chemical make up as the first polymer. The first polymer may form a continuous phase and the second polymer may form a discrete phase within the continuous phase. The discrete phase may be composed substantially of the second polymer's discrete phase segments. At least some of the second polymer's anchor segments may partially or completely phase-separate out from the discrete phase into the continuous phase. The second polymer's anchor segments may tend to facilitate energy transfer between continuous phase and discrete phase, thereby improving fracture toughness under biological conditions. Furthermore, discrete phase segments of the second polymer can also accelerate the degradation rate of the first polymer.

Figure 1B:
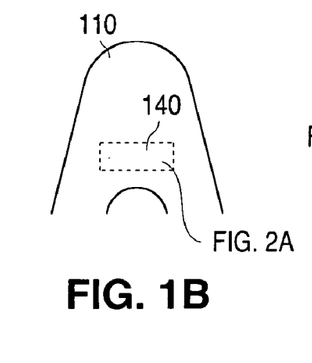
Figure 2A:
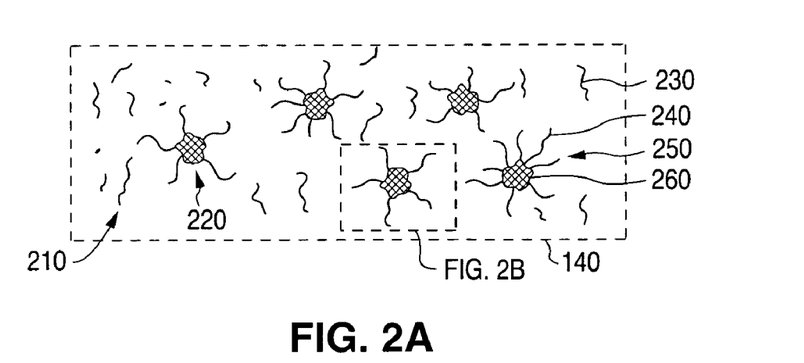
FIG. 2a depicts a close-up view of the strut of FIG. 1b showing a continuous phase and a discrete phase.

FIG. 1b depicts a close-up view of a sidewall of a segment 110 of strut 105 depicted in FIG. 1a. FIG. 2a depicts a microscopic view of a portion 140 of segment 110 of the strut as depicted in FIG. 1b. As depicted in FIG. 2a, portion 140 includes a continuous phase 210 and a discrete phase 220. According to the invention, there is sufficient interfacial adhesion to provide good energy transfer between continuous phase 210 and discrete phase 220 to improve fracture toughness in a device under biological conditions.

As depicted, continuous phase 210 includes a first polymer 230. Dispersed throughout continuous phase 210 is discrete phase 220. Discrete phase 220 includes discrete phase segments 260 of second polymer 250. Discrete phase segments 260 may make up all or a substantial portion of discrete phase 220. It should also be understood by those skilled in the art that some discrete phase segments 260 may not lie entirely in the discrete phase 220, although a substantial portion of discrete phase segments 260 lie within discrete phase 220.

As described above, first polymer can be a polymer that is relatively brittle at biological conditions and/or a degradation rate slower than an ideal range. First polymer 230 may be brittle at biological conditions with a $T_g$ above body temperature. First polymer 230 of continuous phase 210 may be a lactide-based polymer such as PLLA. Under biological conditions, PLLA tends to be brittle and substantially crystalline. "Lactide-based polymer" refers to a polymer containing predominantly lactide moieties.

Figure 2B:
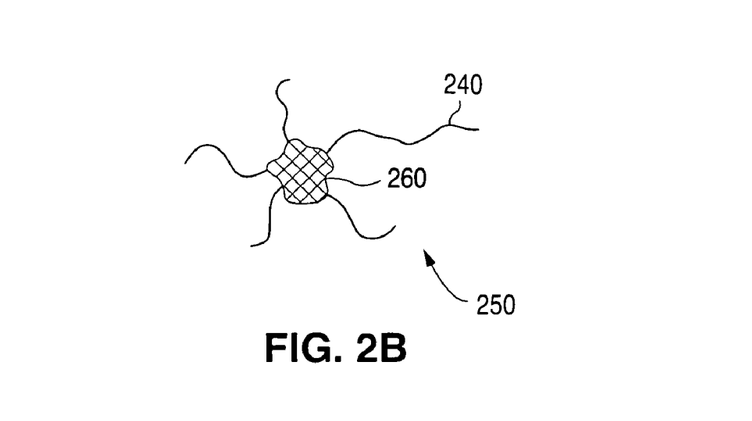
FIG. 2b depicts a close-up view of a second polymer as shown in FIG. 2a that makes up the discrete phase.

Second polymer 250 further includes one or more anchor segments 240 that are of the same or substantially the same chemical make up as first polymer 230 of continuous phase 210. FIG. 2b depicts a close-up view of a second polymer 250 having anchor segments 240 as depicted in FIG. 2a. Because anchor segments 240 are designed to have the same or substantially the same chemical make up as first polymer 230 of continuous phase 210, anchor segments 240 are miscible with continuous phase 210. Thus, anchor segments 240 tend to phase separate out from discrete phase 220 into continuous phase 210, which enhances adhesion between discrete phase 220 and continuation phase 210. Therefore, anchor segments 240 tie or anchor discrete phase 220 to continuous phase 210. In one embodiment, the molecular weight of anchor segments 240 may be higher than its entanglement molecular weight. For example, entanglement molecular weight for PLLA is about 17,000 g/mmol.

In one embodiment, continuous phase 210 is made up of 10% glycolide and 90% PLLA, and anchor segments 240 of second polymer 250 are also made up of 10% glycolide and 90% PLLA. By selecting anchor segments 240 to have the same or substantially the same chemical make up as continuous phase 210, the interfacial adhesion between discrete phase and continuous phase is enhanced since the anchor segments 240 are miscible with continuous phase 210 and phase separate into continuous phase 210. Discrete phase 220 is thereby anchored to continuous phase 210 by anchor segments 240, increasing adhesion between phases and fracture toughness in the device.

In one embodiment, discrete phase segments 260 may be second polymer 250 is selected to provide faster degradation, higher fracture toughness, and/or more flexibility (such as being more rubbery) under biological conditions. In some embodiments, discrete phase segments 260 of second polymer 250 are substantially or entirely amorphous. Discrete phase segments 260 of second polymer 250 may also be selected so that the polymer in the discrete phase has a $T_g$ less than a body temperature. Tying or anchoring of discrete phase 220 to continuous phase 210 with anchor segments 240 results in a substantial increase in interfacial adhesion and energy transfer between continuous phase 210 and discrete phase 220. A substantial increase in interfacial adhesion and energy transfer between phases results in higher fracture toughness in structural element 110 of stent 100 compared to first polymer 230 of continuous phase 210.

In some embodiments, discrete phase segments 260 of second polymer 250 can increase the degradation rate of discrete phase 220. In these embodiments, discrete phase segments may have a higher degradation rate as compared to first polymer 230 of continuous phase 210. Discrete phase segments 260 result in rapid degradation rate of discrete phase 220. In one embodiment, discrete phase segments 260 degrade to acidic fragments that facilitate degradation of discrete phase 220, which also facilitates degradation of continuous phase 210. In another embodiment, discrete phase segments 260 degrade by hydrolysis to form hydrophilic products that increase the equilibrium level of moisture in discrete phase 220, which facilitates the degradation of discrete phase 220, which may also work to facilitate degradation of continuous phase 210.

In one embodiment, the second polymer is poly(L-lactide)-b-poly(glycolide-co-ϵ-caprolactone). In another embodiment, the second polymer is poly(glycolide-co-ϵ-caprolactone)-b-poly(L-lactide). In one embodiment of a blend, the continuous phase is primarily or completely PLLA, and the second polymer is made up of discrete phase segments of glycolide ("GA") and caprolactone ("CL") monomer. Discrete phase segments of GA and CL such as poly(glycolide-co-caprolactone)copolymer segments impart a rapid degradation rate on the second polymer due to the glycolide and higher fracture toughness due to the caprolactone. (For purposes of convenience, discrete phase segments are referred to herein as poly(glycolide-co-caprolactone), although poly(caprolactone-co-glycolide)copolymer segments are also contemplated). Poly(glycolide-co-caprolactone) discrete phase segments can have alternating or random GA and CL monomers. $T_g$ of the poly(glycolide-co-caprolactone) segments can be tuned to a desired value by adjusting the ratio of glycolide and caprolactone monomers. For example, $T_g$ of the discrete phase may be engineered to be less than a body temperature to provide a more flexible discrete phase under biological conditions.

The glycolide-based functional groups in the discrete phase have acidic degradation products that enhance degradation of the discrete phase, which facilitates degradation of the continuous PLLA phase. In addition, the degradation products of glycolide are hydrophilic, which increase the equilibrium level of moisture in the polymer. Both the acidic and hydrophilic properties of the degradation products in glycolide increase the degradation rate of an implantable medical device fabricated from the polymer blend. In addition, as the poly(glycolide-co-caprolactone) discrete phase segments erode, a porous structure is created, allowing more moisture into the polymer which further increases the degradation rate of the discrete phase, also facilitating degradation of the continuous phase.

In one embodiment, the second polymer may have anchor segments made up of PLLA. The PLLA blocks are miscible with PLLA continuous phase. Because PLLA blocks are of the same or substantially the same chemical composition as the continuous phase, they are miscible with PLLA continuous phase and phase-separate from discrete phase into continuous phase. The miscibility of PLLA anchor blocks with PLLA continuous phase provides good interfacial energy between the discrete phase and the continuous phase. PLLA anchor blocks bind poly(L-lactide)-b-poly(glycolide-co-ϵ-caprolactone) or poly(glycolide-co-ϵ-caprolactone)-b-poly (L-lactide)copolymer to the continuous phase. The anchor blocks facilitate energy transfer between the continuous phase and the discrete phase when a device fabricated from the blend is placed under stress. It is believed that when a device is placed under stress, the discrete phase will absorb energy when a fracture starts to propagate through a structural element. As a result, fracture toughness of the continuous phase is increased. Crack propagation through the continuous phase may then be reduced or inhibited.

In one embodiment, a blend for use in fabricating the implantable medical device may include from about 60 to 99 wt %, more narrowly 80 to 95 wt % of the first polymer having the chemical structure:

from about 1 to 40 wt %, or more narrowly 5 to 20 wt % of second polymer having the chemical structure:

In some embodiments, Z is a substantially or completely amorphous polymer. $T_g$ of Z may be made to be below body temperature. $T_g$ of Z may also be made to degrade into fragments at least some of which are acidic. First polymer forms continuous phase while discrete phase segments Z of second polymer forms discrete phase within continuous phase. The "p" segment of the second polymer phase-separates out from discrete phase into the continuous phase.

In one embodiment, the second polymer has the chemical structure:

In one embodiment, the continuous phase is substantially crystalline. In this embodiment, "p" segments phase separate out of the discrete phase into the substantially crystalline continuous phase.

Z can make up discrete phase segments of the second polymer. Z may be made of a rubbery material. Z may have a Young's modules at 6-8 KSi. Z may also have two glass transition temperatures at about −20° C. and about 30° C. Z can also be made to be amorphous. Upon hydrolysis, Z can be made to form hydrophilic fragments. In one embodiment, Z is poly(glycolide-co-caprolactone), which degrades to form acidic and hydrophilic fragments that increase the degradation rate of second polymer having the above chemical structure.

In one embodiment, a polymer blend for fabricating an implantable medical device may further include a rapidly eroding polymer having discrete phase segments without anchor segments. In this embodiment, the first polymer with anchor segments is used as a compatibilizer. The discrete phase may include at least two components (1) the rapidly eroding polymer including discrete phase segments without anchor segments and (2) a polymer with discrete phase segments and anchor segments. In one embodiment, (1) may be a substantial portion of the discrete phase and (2) may be included to facilitate the adhesion of discrete phase with continuous phase.

In one embodiment, second polymer consists essentially of poly(L-lactide)-b-poly(glycolide-co-ϵ-caprolactone)copolymer, which can be added to a mixture of poly(L-lactide) and poly(glycolide-co-caprolactone)copolymer to form a ternary blend. In another embodiment, the second polymer consists essentially of poly(glycolide-co-ϵ-caprolactone)-b-poly(L-lactide)copolymer, which can be added to a mixture of poly(L-lactide) and poly(glycolide-co-ϵ-caprolactone)copolymer to form a ternary blend. In such embodiments, the discrete phase may include poly(glycolide-co-caprolactone)copolymer and poly(glycolide-co-caprolactone) segments of second polymer, poly(glycolide-co-ϵ-caprolactone)-b-poly(L-lactide) while the continuous phase may include poly(L-lactide). Such ternary blends according to the invention further improve degradation and toughness of a construct.

In one embodiment, a blend includes about 5-25 wt % of poly(glycolide-co-caprolactone)copolymer and about 0.5-2 wt % of second polymer of poly(L-lactide)-b-poly(glycolide-co-ϵ-caprolactone)copolymer in a matrix of about 75-95 wt % poly(L-lactide). In this embodiment, poly(L-lactide)-b-poly(glycolide-co-ϵ-caprolactone)copolymer acts as a compatibilizer or dispersant to increase the interfacial adhesion between discrete and continuous phases. The poly(L-lactide)-b-poly(glycolide-co-ϵ-caprolactone)copolymer of this invention can be used as a compatibilizer for blending poly(L-lactide) of the continuous phase with poly(glycolide-co-caprolactone)copolymer of the discrete phase. The ternary polymer blend can be prepared by solution blending or melt blending.

In one embodiment, a blend includes about 5-25 wt % of poly(glycolide-co-caprolactone)copolymer and about 0.5-2 wt % of second polymer of poly(glycolide-co-ϵ-caprolactone)-b-poly(L-lactide)copolymer in a matrix of about 75-95 wt % poly(L-lactide). In this embodiment, poly(glycolide-co-ϵ-caprolactone)-b-poly(L-lactide)copolymer acts as a compatibilizer or dispersant to increase the interfacial adhesion between discrete and continuous phases. The poly(glycolide-co-ϵ-caprolactone)-b-poly(L-lactide)copolymer of this invention can be used as a compatibilizer for blending poly(L-lactide) of the continuous phase with poly(glycolide-co-caprolactone)copolymer of the discrete phase. The ternary polymer blend can be prepared by solution blending or melt blending.

In one embodiment, the invention provides a method of forming poly(glycolide-co-ϵ-caprolactone)-b-poly(L-lactide)copolymer. In this embodiment, the method may include forming poly(glycolide-co-caprolactone) segments first by mixing glycolide monomers, caprolactone monomers, and a solvent to form a solution. In the solution, the glycolide and caprolactone monomers may react to form poly(glycolide-co-caprolactone). The method also includes adding L-lactide monomers to allow L-lactide monomers to react with poly(glycolide-co-caprolactone) to form poly(glycolide-co-ϵ-caprolactone)-b-poly(L-lactide).

In one embodiment, the L-lactide monomers may react with poly(glycolide-co-caprolactone) in the solution to form poly(glycolide-co-ϵ-caprolactone)-b-poly(L-lactide).

In another embodiment, the L-lactide monomers may react with poly(glycolide-co-caprolactone) in a solution having another solvent(s) to form poly(glycolide-co-ϵ-caprolactone)-b-poly(L-lactide).

In one embodiment, the method may further include adding L-lactide and glycolide monomers to allow the L-lactide and glycolide monomers to react to form poly(glycolide-co-ϵ-caprolactone)-b-poly(lactide-co-glycolide). In one embodiment, the L-lactide and glycolide monomers react in the solution to form poly(glycolide-co-ϵ-caprolactone)-b-poly(lactide-co-glycolide). Alternatively, the L-lactide and glycolide monomers react in a solution having another solvent(s) to form poly(glycolide-co-ϵ-caprolactone)-b-poly(lactide-co-glycolide).

The poly(glycolide-co-ϵ-caprolactone)-b-poly(L-lactide) copolymer and poly(L-lactide)-b-poly(glycolide-co-ϵ-caprolactone)copolymer can be formed by solution-based polymerization. In solution based polymerization, all the reactive components involved in the polymerization reaction are dissolved in solvent. Other methods used to form poly(glycolide-co-ϵ-caprolactone)-b-poly(L-lactide)copolymer or poly(L-lactide)-b-poly(glycolide-co-ϵ-caprolactone)copolymer are also possible, such as, without limitation, melt phase polymerization. In one embodiment, the poly(glycolide-co-ϵ-caprolactone)-b-poly(L-lactide)copolymer or poly(L-lactide)-b-poly(glycolide-co-ϵ-caprolactone)copolymer can be formed by providing a solvent system to keep the poly(glycolide-co-caprolactone)copolymer in solution so that the copolymer can be further copolymerize with L-lactide.

In one embodiment, poly(glycolide-co-ϵ-caprolactone)-b-poly(L-lactide) is formed by reacting poly(glycolide-co-caprolactone)copolymer, which is swollen with a solvent, with L-lactide monomers such that it is not necessary to dissolve the poly(glycolide-co-caprolactone) in a solvent to form poly(glycolide-co-ϵ-caprolactone)-b-poly(L-lactide). In one embodiment, after poly(glycolide-co-caprolactone)copolymer is formed, poly(glycolide-co-caprolactone)copolymer is not dissolved in the solvent; rather, the poly(glycolide-co-caprolactone)copolymer swells in the solvent in order to facilitate polymerization of poly(glycolide-co-ϵ-caprolactone)copolymer with L-lactide monomers. That is, when GA and CL copolymerize, the resulting poly(glycolide-co-caprolactone)copolymer swells in the solvent, providing a means by which L-lactide monomers later added to the system can copolymerize with the swollen poly(glycolide-co-caprolactone)copolymer.

In one embodiment, poly(L-lactide)-b-poly(glycolide-co-ϵ-caprolactone)copolymer can be formed, first, by mixing the poly(L-lactide) monomers with a solvent to form a solution. Once poly(L-lactide) is formed, glycolide monomers and caprolactone monomers are added to the poly(L-lactide)copolymer to form poly(L-lactide)-b-poly(glycolide-co-ϵ-caprolactone)copolymer. In embodiment, the glycolide monomers and caprolactone monomers are added to allow glycolide and caprolactone monomers to react with poly(L-lactide) in the solution to form poly(L-lactide)-b-poly(glycolide-co-ϵ-caprolactone)copolymer. Alternatively, the glycolide monomers and caprolactone monomers are added to allow glycolide and caprolactone monomers to react with poly(L-lactide) to form poly(L-lactide)-b-poly(glycolide-co-ϵ-caprolactone)copolymer in a solution having a different solvent(s).

In one embodiment, the solvent for use in synthesizing the copolymer is devoid of alcohol functional groups. Such groups may act as initiators for chain growth in the polymer Solvents used to synthesize the copolymer include, but are not limited to, chloroform, toluene, xylene, and cyclohexane. Initiators to facilitate the synthesis of the copolymer include, but are not limited to, dodecanol, ethanol, ethylene glycol, and polyethylene glycol. Catalysts used to facilitate the synthesis of the copolymer include, but are not limited to, stannous octoate and stannous trifluoromethane sulfonate.

It should be understood by those skilled in the art that continuous phase and discrete phase polymers other than those disclosed above and exemplified below may be used to create polymer blends of this invention for use in fabricating an implantable medical device. For example, discrete phase segments of the second polymer can be formed by polymerizing other types of monomers that provide the polymer with an increase in degradation rate or an increase in fracture toughness. For example, trimethylene carbonate monomers can be polymerized with glycolide to form discrete phase segments. Further, anchor segments and the first polymer of continuous phase can be formed of polymers other than L-lactide, such as, for example, D,L-lactide.

A stent fabricated using a polymer blend of this invention can be medicated with an active agent. A medicated stent may be fabricated by coating the surface of the polymeric scaffolding made from the blend with a polymeric carrier that includes a bioactive agent. A bioactive agent can also be incorporated into a polymeric scaffolding made from the blend.

EXAMPLES

The Examples below are provided by way of illustration only and not by way of limitation. The prophetic and actual Examples illustrate formation of poly(L-lactide)-poly(glycolide-co-ϵ-caprolactone) and poly(glycolide-co-ϵ-caprolactone)-b-poly(L-lactide)copolymer for use in fabricating an implantable medical device. This copolymer consists of two segments: the poly(glycolide-co-caprolactone) discrete phase segments, and the poly(L-lactide) anchor blocks. The parameters and data are not to be construed to limit the scope of the embodiments of the invention.

Example 1

Figure 3:
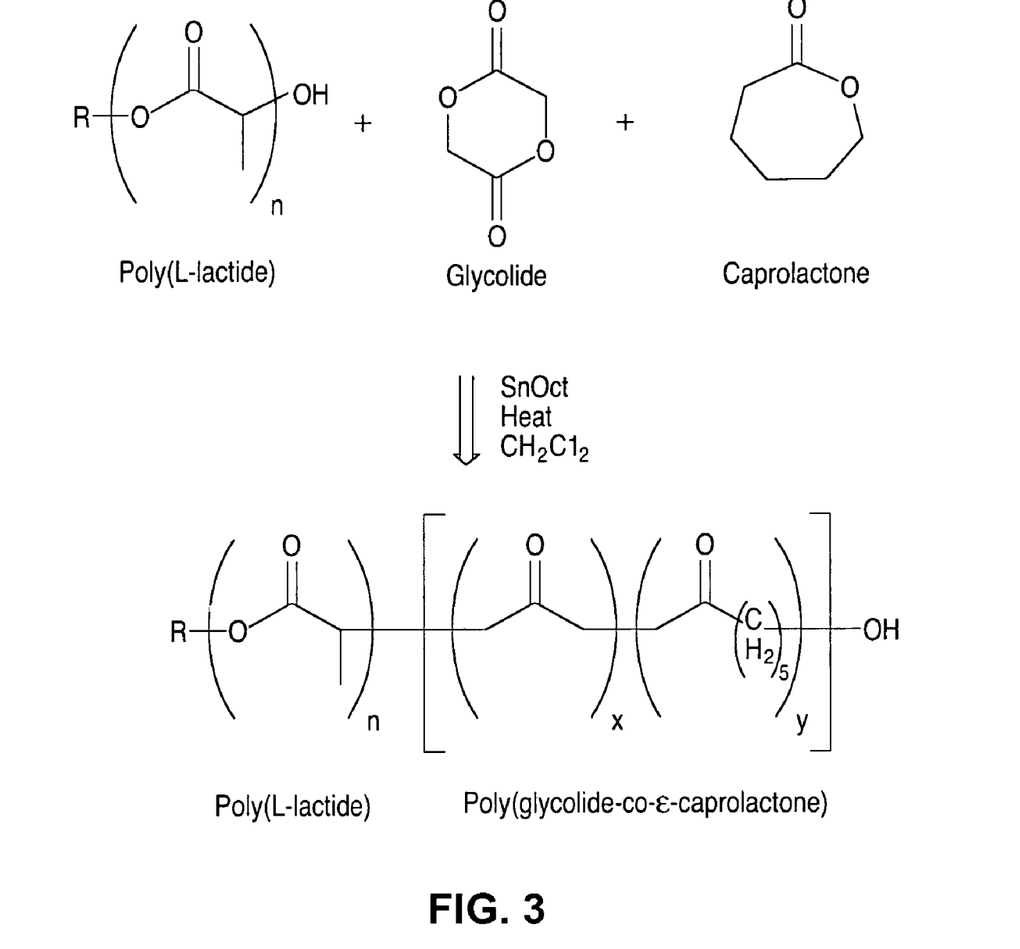
FIG. 3 illustrates the synthesis of poly(glycolide-co-ε-caprolactone)-b-poly(L-lactide)copolymer according to one embodiment of the invention.

Poly(glycolide-co-ϵ-caprolactone)-b-poly(L-lactide)copolymer was synthesized by forming the poly(glycolide-co-caprolactone) segments first. Then, poly(glycolide-co-caprolactone) is used to initiate polymerization of L-lactide. FIG. 3 illustrates the synthesis of poly(glycolide-co-ϵ-caprolactone)-b-poly(L-lactide)copolymer according to this embodiment. FIG. 3 shows that glycolide and caprolactone monomers were combined in the presence of an alcohol initiator, catalyst, and solvent to form poly(glycolide-co-caprolactone). L-lactide was then added to the mixture to form the poly(glycolide-co-ϵ-caprolactone)-b-poly(L-lactide)copolymer.

Chloroform, toluene, xylene, or cyclohexane can be used as the solvent. The reactants can be dissolved in the solvent during the early stages of polymerization. The solvent can be removed at higher temperature to increase polymerization rate. Initiators can include dodecanol and ethanol.

Catalysts can include stannous octoate and/or stannous trifluoromethane sulfonate.

The following two examples describe the synthesis of poly(glycolide-co-ϵ-caprolactone)-b-poly(L-lactide)copolymer for two target molecular weights. In each procedure, glycolide ("GA"), caprolactone ("CL"), and L-lactide ("LLA") are used as monomers, stannous octoate as the catalyst, dodecanol as the initiator and xylene as the solvent.

Example 1a

The following steps describe a polymerization procedure that was used to form poly(glycolide-co-ϵ-caprolactone)-b-poly(L-lactide) with a target molecular weight of 150 g/mole:

Step 1: A 2-L reaction kettle equipped with mechanical stirring was placed in a glove box which was filled with high purity nitrogen. The reaction kettle was preheated to remove moisture.

Step 2: 100 g GA, 100 g CL, 0.44 mL dodecanol, 200 ml xylene and 0.56 mL stannous octoate were added to the reaction kettle, the GA being added in 4 portions in two-hour intervals. The mixture was stirred at 120° C. for 53 hours.

Step 3: 100 g LLA was then added into reaction kettle and the reaction continued for another 68 hours.

Step 4: 1.5 L $CHCl_3$ was then added to reaction kettle to dilute the final product. The reaction mixture was poured into 4-L methanol upon which the product precipitated. Then, the product was dried in vacuum at 80° C. until constant weight.

Example 1b

At the end of Step 2 in Example 1a, a small amount sample was taken out of the reaction kettle, and Nuclear Magnetic Resonance ("NMR"), Differential Scanning Calorimeter, and tensile testing was performed. Neither GA nor CL monomer peaks were found in the H-NMR, which proved that both GA and CL monomers had been consumed to form PGA-co-PCL discrete phase copolymer after a 53-hour reaction. ($^1$H-NMR of the end product of Step 3 in Example 2a showed that more than 98% LLA monomer had been consumed to form the pure poly(L-lactide) block on the poly(glycolide-co-ε-caprolactone)-b-poly(L-lactide)copolymer. The formed poly(glycolide-co-caprolactone) discrete phase copolymer was a rubbery material with a relatively low Young's modules of 6.7 KSi and glass transition temperatures at −20° C. and 30° C.

Example 1c

The following steps were performed to synthesize poly (glycolide-co-ε-caprolactone)-b-poly(L-lactide)copolymer at a target molecular weight of 600 g/mol:

Step 1: A 2-L reaction kettle was preheated to remove moisture. The reaction kettle with mechanical stirring was placed into a glove box which was filled with high purity nitrogen.

Step 2: 130 g GA, 70 g CL, 0.11 mL dodecanol, 200 mL xylene and 0.56 mL stannous octoate were added to the reaction kettle, the GA being added in 4 portions in two-hour intervals. The mixture was then stirred at 120° C. for 72 hours.

Step 3: LLA was then added to the reaction kettle and the reaction continued for another 72 hours.

Step 4: 1.5 L $CHCl_3$ was then added to the reaction kettle to dilute the final product. Finally, all the reaction solution was poured in 4-L methanol upon which the product was precipitated, and the product was filtered and dried in vacuum at 80° C. to constant weight.

Example 1d

Poly(glycolide-co-caprolactone)copolymer was also be synthesized by first placing GA and CL monomers, initiator (dodecanol), catalyst ($Sn(Oct)_2$ or stannous trifluoromethane sulfonate or "$Sn(OTf)_2$") and xylene in a reactor, as in Example 2a. The poly(glycolide-co-caprolactone) discrete phase copolymer was then precipitated in methanol, and dried in a vacuum oven. To precipitate the poly(glycolide-co-caprolactone) discrete phase copolymer, the poly(glycolide-co-caprolactone) discrete phase copolymer formed can be used in a ternary blend or used to form poly(glycolide-co-ε-caprolactone)-b-poly(L-lactide).

The molecular weight of the poly(glycolide-co-caprolactone) discrete phase copolymer was controlled by the molar ratio of monomers to initiator. The degradation rate and toughness were controlled by the molar ratio of GA to CL.

Example 2

Figure 4:
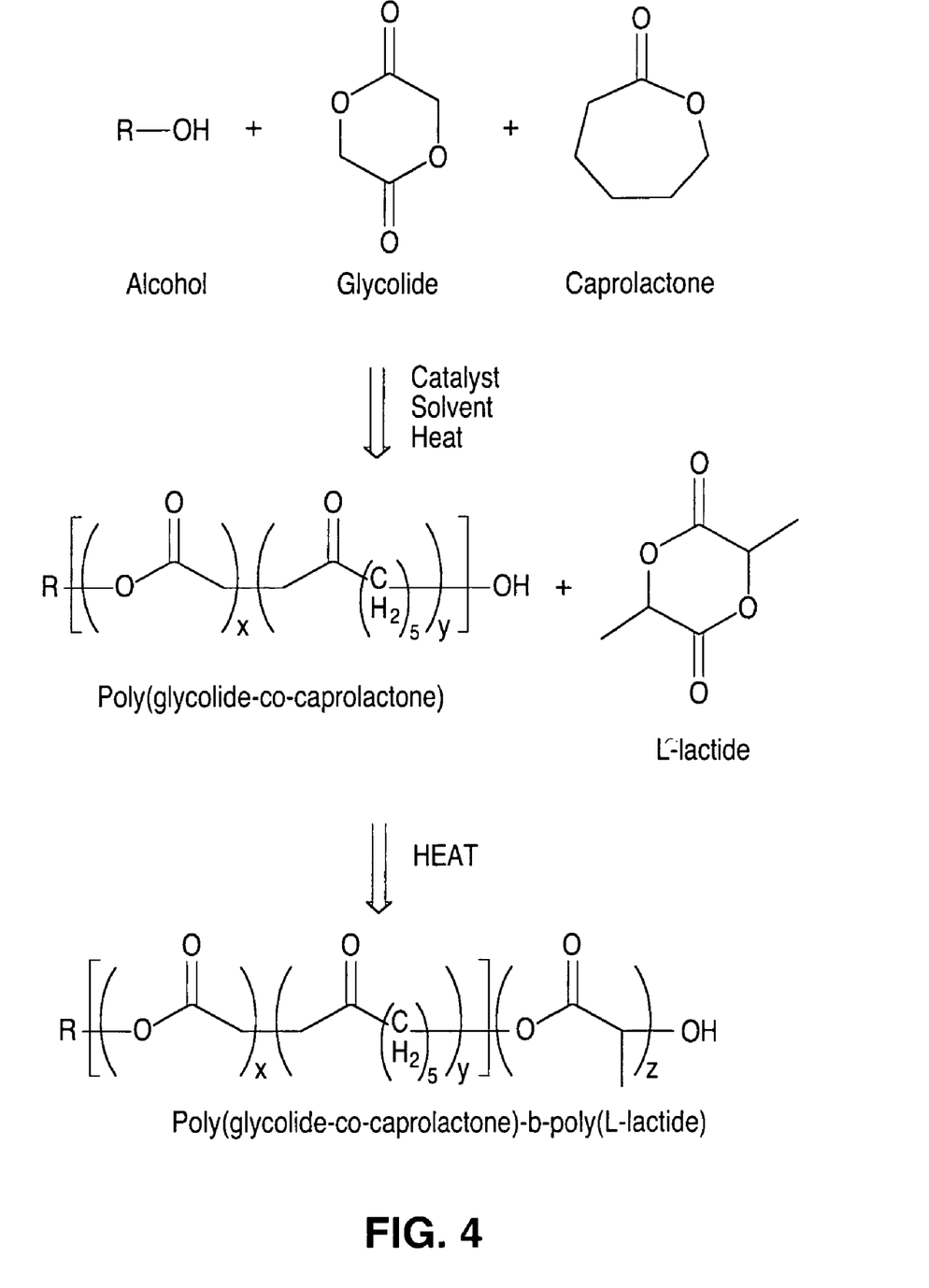
FIG. 4 illustrates the synthesis of poly(L-lactide)-b-poly(glycolide-co-ε-caprolactone)copolymer according to another embodiment of the invention.

Poly(L-lactide)-b-poly(glycolide-co-ε-caprolactone)copolymer can be synthesized by forming the PLLA segment first, and then adding GL and CL monomers to form the copolymer. FIG. 4 illustrates the synthesis of poly(L-lactide)-b-poly(glycolide-co-ε-caprolactone)copolymer according to this embodiment. To synthesize the poly(L-lactide), L-lactide (monomer), alcohol (initiator), catalyst, and a solvent can be added to a reactor vessel. Once the poly(L-lactide) has formed, GA, CL and optionally more solvent can be added into reactor. NMR or GPC can indicate when the first poly(L-lactide) blocks are formed or mass conversion of L-lactide monomers.

Chloroform, toluene, xylene, or cyclohexane can be used as the solvent. The reactants can be dissolved in the solvent during the early stages of polymerization. The solvent can be removed at higher temperature to increase polymerization rate. Initiators can include dodecanol and/or ethanol.

Catalysts can include stannous octoate and stannous trifluoromethane sulfonate.

The temperature of the reactor was about or above 100° C. when xylene or toluene is used as the solvent, and about or below 80° C. when cycloxane, chloroform or methylene chloride was used.

The following describes a polymerization procedure that was used to form poly(L-lactide)-b-poly(glycolide-co-ε-caprolactone). The solvent was toluene, the initiator was dodecanol, and the catalyst was stannous octoate.

Step 1: A 2-L 4-neck reactor with mechanical stirring rod was placed into a heating mantle, then into a glove box.

Step 2: The glove box was purged in nitrogen, deflated, and purged again. This step was repeated 3 times to remove all oxygen and moisture from glove box which finally was filled with nitrogen.

Step 3: 50 g of L-Lactide, 0.186 g of 1-dodecanol, and 50 ml toluene were added to the flask.

Step 4: 40 mg stannous octoate was added, and the temperature was increased to 100° C.

Step 5: After 22 hours, 100 mL of toluene, 50 g caprolactone, and 50 g glycolide were added. Glycolide was added in three steps: 25 g glycolide was added together with CL. Then, 12.5 g glycolide was added 2 hours later, followed by 12.5 g glycolide two hours after that.

Step 6: After 48 hours, the product was precipitated from methanol and was dried in a vacuum overnight.

While particular embodiments of the present invention have been shown and described, it will be obvious to those skilled in the art that changes and modifications can be made without departing from this invention in its broader aspects.

The invention claimed is:

1. An implantable medical device comprising:
   a structural element, wherein the structural element includes:
   a continuous phase comprising a first polymer;
   a discrete phase within the continuous phase, wherein the discrete phase comprises a second polymer including discrete phase segments;
   the second polymer further includes anchor segments that have the same or substantially the same chemical make up as the first polymer of the continuous phase, and at least some of the anchor segments have partially or completely phase-separated from the discrete phase into the continuous phase.

2. The device according to claim 1, wherein the implantable medical device is a stent.

3. The device according to claim 1, wherein the first polymer is a biodegradable polymer.

4. The device according to claim 1, wherein the discrete phase segments have a $T_g$ below body temperature.

5. The device according to claim 1, wherein the discrete phase is more flexible than the continuous phase at body temperature.

6. The device according to claim 1, wherein the anchor segments are miscible with the first polymer.

7. The device according to claim 1, wherein the first polymer substantially or completely comprises poly(L-lactide).

8. The device according to claim 1, wherein the discrete phase segments comprise poly(glycolide-co-ϵ-caprolactone) copolymer.

9. The device according to claim 1, wherein the second polymer comprises poly(glycolide-co-ϵ-caprolactone)-b-poly(L-lactide).

10. The device according to claim 1, wherein 1 to 40 wt % of the structural element comprises the second polymer.

11. The device according to claim 1, wherein 5-20 wt % of the structural element comprises the second polymer.

12. The device according to claim 1, wherein the discrete phase segments degrade to acidic fragments.

13. The device according to claim 1, wherein the discrete phase segments degrade to hydrophilic fragments.

14. An implantable medical device, comprising a blend including:
a structural element having:
about 60 to about 99 wt % of a first polymer, wherein the first polymer forms a continuous phase; and
about 1 to about 40 wt % of a second polymer, the second polymer forming a discrete phase within the continuous phase, wherein the second polymer having a $T_g$ below body temperature comprises discrete phase segments that degrade to acidic fragments,
the second polymer also comprises anchor segments having the same or substantially the same chemical make up as the continuous phase, wherein the anchor segment has phase-separated out from the discrete phase into the continuous phase.

15. The device according to claim 14, wherein the first polymer is poly(L-lactide).

16. The device according to claim 14, wherein the second polymer is poly(glycolide-co-ϵ-caprolactone)-b-poly(L-lactide).

17. The device according to claim 14, wherein the anchor segment is selected from the group consisting of poly(L-lactide), materials that are miscible in poly(L-lactide), or both.

18. An implantable medical device, comprising a blend including:
a structural element having:
about 60 to about 99 wt % of a first polymer, wherein the first polymer forms a continuous phase;
about 0.2 to about 5 wt % of a second polymer, the second polymer forming a discrete phase within the continuous phase, the second polymer comprising discrete phase segments and anchor segments, wherein anchor segments have the same or substantially the same chemical make up as the first polymer of the continuous phase and have phase-separated out from the discrete phase into the continuous phase; and
about 1 to about 40 wt % of a third polymer having a $T_g$ below body temperature consists essentially of discrete phase segments, wherein the third polymer degrades into fragments at least some of which are acidic.

19. The device according to claim 18, wherein the second polymer has at a $T_g$ below body temperature.

20. The device according to claim 18, wherein the second polymer degrades to acidic fragments.

21. The device according to claim 18, wherein the first polymer is poly(L-lactide).

22. The device according to claim 18, wherein the second polymer is poly(glycolide-co-ϵ-caprolactone)-b-poly(L-lactide) copolymer.

23. The device according to claim 18, wherein the anchor segments are poly(L-lactide).

24. The device according to claim 18, wherein the third polymer is poly(glycolide-co-ϵ-caprolactone) copolymer.

25. A composition comprising:
a continuous phase comprising a first polymer;
a discrete phase within the continuous phase, wherein the discrete phase comprises a second polymer including discrete phase segments;
the second polymer further includes anchor segments that have the same or substantially the same chemical make up as the first polymer of the continuous phase, and at least some of the anchor segments have partially or completely phase-separated from the discrete phase into the continuous phase.

26. The composition to claim 25, wherein the first polymer is a biodegradable polymer.

27. The composition to claim 25, wherein the anchor segments are miscible with the first polymer.

28. The composition to claim 25, wherein the first polymer substantially or completely comprises poly(L-lactide).

29. The composition to claim 25, wherein the fast eroding segments comprise poly(glycolide-co-ϵ-caprolactone) copolymer.

30. The composition to claim 25, wherein the second polymer comprises poly(glycolide-co-caprolactone)-b-poly(L-lactide).

31. The composition to claim 25, wherein the discrete phase further comprises a polymer consisting essentially of discrete phase segments.

32. The composition to claim 25, wherein 1-40 wt % of the structural element comprises the second polymer.

33. The composition to claim 25, wherein the discrete phase segments degrade to acidic fragments.

34. The composition to claim 25, wherein the discrete phase segments degrade to form degradation products that are hydrophilic.

35. The composition to claim 25, wherein the discrete phase segments are formed by polymerizing at two or more of the following monomers in any proportion: glycolide, caprolactone, and trimethylene carbonate.

36. A method of forming a copolymer comprising:
mixing glycolide monomers, caprolactone monomers, and a solvent to form a solution, wherein the glycolide and caprolactone monomers react in the solution to form poly(glycolide-co-ϵ-caprolactone); and
adding L-lactide monomers to allow L-lactide monomers to react with poly(glycolide-co-caprolactone) to form poly(glycolide-co-ϵ-caprolactone)-b-poly(L-lactide).

37. A method of forming a copolymer comprising:
mixing glycolide monomers, caprolactone monomers, and a solvent to form a solution, wherein the glycolide monomers and caprolactone monomers react in the solution to form poly(glycolide-co-ε-caprolactone);

adding L-lactide monomers to allow L-lactide monomers to react with the poly(glycolide-co-ε-caprolactone) to form poly(glycolide-co-ε-caprolactone)-b-poly(L-lactide); and adding L-lactide and glycolide monomers to allow the L-lactide and glycolide monomers to react to form poly(glycolide-co-ε-caprolactone)-b-poly(L-lactide-co-glycolide).

38. The method according to claim 37, wherein the L-lactide monomers are allowed to react with the poly(glycolide-co-ε-caprolactone) in the presence of a solvent, wherein the solvent is the same or different solvent used to form the solution.

39. The method according to claim 37, wherein the solvent is a blend of solvents.

40. The method according to claim 37, wherein the solvent is devoid of alcohol functional groups.

41. The method according to claim 37, wherein the solvent is selected from the group consisting of chloroform, toluene, xylene, cyclohexane, and any mixture thereof in any proportion.

42. The method according to claim 37, wherein the solution comprises an initiator selected from the group consisting of dodecanol, ethanol, ethylene glycol, polyethylene glycol, and any mixtures thereof.

43. The method according to claim 37, wherein the solution comprises a catalyst selected from the group consisting of stannous octoate, stannous trifluoromethane sulfonate, and any mixtures thereof.

44. A method of forming a copolymer comprising:
mixing L-lactide monomers with a solvent to form a solution, wherein L-lactide polymerizes to form poly(L-lactide);

adding glycolide monomers and caprolactone monomers with the poly(L-lactide) to allow the glycolide monomers and caprolactone monomers to react with the poly(L-lactide) to form poly(L-lactide)-b-poly(glycolide-co-ε-caprolactone).

45. The method according to claim 44, wherein the glycolide and caprolactone monomers are allowed to react with the poly(L-lactide) in the presence of a solvent, wherein the solvent is the same or different solvent used to form the solution.

46. The method according to claim 44, wherein the solvent is a blend of solvents.

47. The method according to claim 44, wherein the solvent is devoid of alcohol functional groups.

48. The method according to claim 44, wherein the solvent is selected from the group consisting of chloroform, toluene, xylene, cyclohexane, and any mixture thereof in any proportion.

49. The method according to claim 44, wherein the solution comprises an initiator selected from the group consisting of dodecanol, ethanol, ethylene glycol, polyethylene glycol, and any mixtures thereof.

50. The method according to claim 44, wherein the solution comprises a catalyst selected from the group consisting of stannous octoate, stannous trifluoromethane sulfonate, and any mixtures thereof.

51. A copolymer comprising poly(L-lactide)-b-poly(glycolide-co-ε-caprolactone).

52. A copolymer comprising poly(glycolide-co-ε-caprolactone)-b-poly(L-lactide).

53. A copolymer comprising poly(glycolide-co-ε-caprolactone)-b-poly(lactide-co-glycolide).

* * * * *